United States Patent [19]
Webster

[11] Patent Number: 4,684,258
[45] Date of Patent: Aug. 4, 1987

[54] METHOD AND APPARATUS FOR ENHANCING LASER ABSORPTION SENSITIVITY

[75] Inventor: Christopher R. Webster, Pasadena, Calif.

[73] Assignee: The United States of America as represented by the Administrator of the National Aeronautics and Space Administration, Washington, D.C.

[21] Appl. No.: 760,790

[22] Filed: Jul. 31, 1985

[51] Int. Cl.[4] .............................................. G01N 21/17
[52] U.S. Cl. .................................... 356/409; 250/339; 250/343; 250/373; 356/51; 356/256
[58] Field of Search ...................... 250/339, 343, 373; 356/51, 300, 326, 402, 409, 420, 256; 372/92, 98, 105

[56] References Cited

U.S. PATENT DOCUMENTS

| | | | |
|---|---|---|---|
| 3,435,371 | 3/1969 | White | 372/105 |
| 3,731,224 | 5/1973 | Dienes et al. | 372/33 |
| 3,868,592 | 2/1975 | Yarborough et al. | 372/105 |
| 4,233,569 | 11/1980 | Liu | 372/105 |
| 4,268,800 | 5/1981 | Johnston, Jr. et al. | 372/20 |
| 4,438,517 | 3/1984 | Bobb et al. | 372/99 |

OTHER PUBLICATIONS

Reid et al., *Applied Optics*, vol. 19, No. 19, Oct. 1, 1980, pp. 3349-3354.

Primary Examiner—F. L. Evans
Attorney, Agent, or Firm—Paul F. McCaul; John R. Manning; Thomas H. Jones

[57] ABSTRACT

A simple optomechanical method and apparatus is described for substantially reducing the amplitude of unwanted multiple-interference fringes which often limit the sensitivities of tunable laser absorption spectrometers. An exterior cavity is defined by partially-transmissible surfaces such as a laser exit plate, a detector input, etc. That cavity is spoiled by placing an oscillating plate in the laser beam. For tunable diode laser spectroscopy in the mid-infrared region, a Brewster-plate spoiler allows the harmonic detection of absorptances of $<10^{-5}$ in a single laser scan. Improved operation is achieved without subtraction techniques, without complex laser frequency modulation and without distortion of the molecular lineshape signal. The technique is applicable to tunable lasers operating from UV to IR wavelengths and in spectrometers which employ either short or long pathlengths, including the use of retroreflectors or multipass cells.

19 Claims, 6 Drawing Figures (a)

41

42

(b)

130   150   170   190

DIODE LASER CURRENT (mA)

(a)

(b)

(c)

DIODE LASER FREQUENCY (cm$^{-1}$)

METHOD AND APPARATUS FOR ENHANCING LASER ABSORPTION SENSITIVITY

ORIGIN OF THE INVENTION

The invention described herein was made in the performance of work under a NASA Contract and is subject to the provisions of Public Law 96-517 (35 USC 202) in which the contractor has elected not to retain title.

BACKGROUND OF THE INVENTION

1. Field of the Invention

This invention relates to a method and apparatus for providing enhanced sensitivity in detecting atomic and molecular species of interest through their absorption spectra. For laboratory measurements, spectroscopic studies, White-cell in-situ monitoring and long-path stratospheric monitoring, the species being measured are gases at low pressures. For example, it has been determined that White cells of base pathlength in the range 1.0-4.0 m may be particularly susceptible to unwanted interference fringe generation which reduces the sensitivities attainable using tunable laser absorption techniques. These fringes are caused by multiple reflections of light between any two or more surfaces located within the light-source-to-detector path.

In many applications of tunable diode laser (TDL) spectroscopy to molecular detection, it is not possible to "remove" the molecular gas being measured. The fringes may therefore not be independently recorded and the molecular contribution extracted by subtraction techniques. Any post-detection data-handling technique must use one identity to separate the two contributions.

In accordance with this invention, a Brewster-plate spoiler is oscillated within the passive cavity which is formed outside of the laser resonator's cavity. This passive cavity is formed by the surfaces from which the multiple reflections, and therefore fringe generation occurs. Frequency-related interference effects in a tunable laser absorption spectrum are minimized by this invention.

2. Brief Description of the Prior Art

Tunable diode laser spectrometers are employed for high sensitivity studies. Laboratory and field studies include multipass cell measurements and/or long pathlength atmospheric measurements using retroreflectors. Such devices have been limited in precision measurement sensitivity by the presence of optical interference fringes. When used to measure molecular absorptions smaller than 0.01%, even though optical beam noise is reduced by increased integration time, actual measurement sensitivity is limited by the presence of interference fringes.

The sensitivity of laser absorption measurements is limited by the production of Fabry-Perot interference fringes. Such fringes are generated through multiple beam interferences between optical surfaces located within the source-to-detector path of the spectrometer system. The fringes may result from laser transmission through individual optical elements, such as windows or lenses, or through air and vacuum paths separated by the surfaces of different system elements. Even if very careful optical alignment procedures are practiced, such efforts cannot completely remove interference fringes.

Fringes of peak-to-peak optical depth of a few parts in $10^4$, for example, are produced by surface reflectivities as low as 0.01%. For multipass absorption cells, the problem is more serious due to the increased beam overlap. Multipass absorption attempts to maximize the effective pathlength by increasing the number of optical passes. Thus, multipass systems have increased interference.

Tunable diode laser (TDL) spectrometers are particularly suited to high sensitivity studies, in part because they may be readily frequency-modulated. Harmonic techniques are used to measure molecular absorptions smaller than 0.01%. At this low molecular absorption level, optical beam noise may be reduced by increased integration time. Notwithstanding enhanced tuning of the laser and reduction in optical beam noise, the measurement sensitivity is, nevertheless, limited by the presence of the above-noted optical interference fringes.

Various attempts to improve sensitivity have been made. For example, Reid et al. successfully used a jitter-modulation technique that is described in *Applied Optics*, 19 (1980) p. 3349, in an article entitled "Sensitivity Limits of a Turnable Diode Laser Spectrometer, with Application to the Detection of $NO_2$ at the 100-ppt Level." Reid et al. later developed a two-tone modulation technique disclosed in "Harmonic Detection with Turnable Diode Lasers: Two-Tone Modulation," to reduce optical fringing the latter being published in *Applied Physics B*, 29, (1983) p. 279. A related approach described in "Improvement of Etalon-fringe Immunity in Diode-Laser Derivative Spectroscopy," was taken by Koga et al as reported in *Memoirs of the School of Engineering, Okayama University*, 16, (1981) p. 21. Koga et al. proposed modulating the TDL current with an exponential function approximating an inverse integrated raised cosine profile.

All three of the referenced techniques attack the fringing problem through laser modulation. They use complex modulations which produce harmonic signal sizes and nonconventional linewidths. The complex modulation of this prior art approach makes transformation back to gas concentration measurements unnecessarily difficult. The above-noted prior art is relevant to a general concept of improving a laser's performance. It has limited relevance to this invention.

Tuning a Fabry-Perot cavity using an internal Brewster plate has been previously applied to cw dye lasers as described in "Direct Optical Measurement of Sodium Hyperfine Structure using cw Dye Lasers and an Atomic Beam," by Schuda et al *Applied Physics Letters*, 22, (1973) p. 360. In accordance with this invention, an exterior cavity resonance is defined. Rather than tuning by use of a Brewster plate, as suggested by the above-noted prior art, the exterior cavity is spoiled, in accordance with this invention, by oscillating a plate about an axis 90° to the plane of the laser beam's incidence.

The following patents were deemed relevant to a prior art search on the disclosed invention: U.S. Pat. No. 3,731,224 to Dienes et al.; U.S. Pat. No. 4,268,800 to Johnson, Jr. et al.; U.S. Pat. No. 3,435,371 to A. D. White; U.S. Pat. No. 3,868,592 to Yarborough et al.; U.S. Pat. No. 4,233,569 to Liu; and U.S. Pat. No. 4,438,517 to Bobb et al.

Dienes et al. U.S. Pat. No. 3,731,224 discloses a compensated folded resonator having a Brewster element 21 within the laser cavity for introducing an astigmatic effect which cancels an already existing one due to the resonator mirrors, elements 18 and 19. See Column 3, lines 20-40. The Brewster plate solves a different problem by a different structure than that of the present invention. Furthermore, the folding of spherical mirrors in Dienes et al. U.S. Pat. No. 3,731,224 inherently creates an astigmatic effect within the laser cavity itself. By cancelling that astigmatism, instability in the resonance frequency and reduced laser output power can be overcome. Dienes et al. U.S. Pat. No. 3,731,224 does not have an oscillating plate nor does it correct for interference fringes outside of the laser cavity.

Johnston, Jr. et al. U.S. Pat. No. 4,268,800 discloses, in FIG. 1A, a known prior art use of tipping an inserted glass plate about a small range of angles near Brewster's angle to change the length of optical path in a dye laser cavity to produce a frequency scan. The Brewster plate 30 is mounted within the laser cavity near the vertex of the incident beam and the reflected beam. The Brewster plate 30 is tipped or scanned through a small angle, thereby cancelling the lateral displacement of the incident and reflected beams. See Column 2, lines 20-35. Brewster plate 30 is tipped to selectively tune the laser to a predetermined output frequency. See Column 1, lines 43-67. It should be noted that Johnston, Jr. et al. U.S. Pat. No. 4,268,800 (Column 1, lines 26-29) also lists as background prior art one of the literature references cited above.

U.S. Pat. Nos. 3,435,371, 3,868,592, 4,233,569 and 4,438,517 disclose, as did Johnston, Jr. et al. U.S. Pat. No. 4,268,800, a technique for tuning a laser. In particular, U.S. Pat. No. 3,868,592 uses a birefringent plate 10 disposed at the Brewster angle for tuning the laser. See Column 3, lines 31-47.

SUMMARY OF THE INVENTION

Briefly, the subject invention comprises a method and apparatus for reducing the amplitude of interference fringes which limit tunable laser absorption sensitivities. A Brewster-plate spoiler is physically oscillated between cavity surfaces which are exterior to the laser's inside cavity. The spoiling cyclically varies the optical path length and creates standing waves in the cavity. In the method and apparatus of this invention, the active laser cavity resonance is not tuned by rotating the Brewster plate in one direction; instead, the exterior or passive cavity resonance is spoiled by oscillating the plate back and forwards about one axis.

For example, a lead-salt diode laser operating in the 7-$\mu$m region may be employed with a single Brewster-plate spoiler to reduce the fringe amplitude by a factor of 30 and also allows the detection of absorptances of $10^{-3}$% in a single laser scan without subtraction techniques, without complex frequency modulation, and without distortion of the molecular lineshape signals. The method and apparatus is likewise applicable to multipass cell spectrometers.

The simple and efficient features of this invention substantially reduce the amplitude of unwanted interference fringes without distortion of the molecular lineshape. Oscillation of a Brewster-plate spoiler according to this invention is applicable to measurements employing tunable lasers of any wavelength. Thus, it finds application in measurements using short pathlengths, long pathlengths with retroreflectors or multipass cells.

BRIEF DESCRIPTION OF THE DRAWINGS

FIG. 5 is a series of graphs comparing a portion of the second-harmonic $N_2O$ spectrum near 1308 cm$^{-1}$ without, and with, the spoiler on.

DETAILED DESCRIPTION OF THE DRAWINGS

Figure 1:
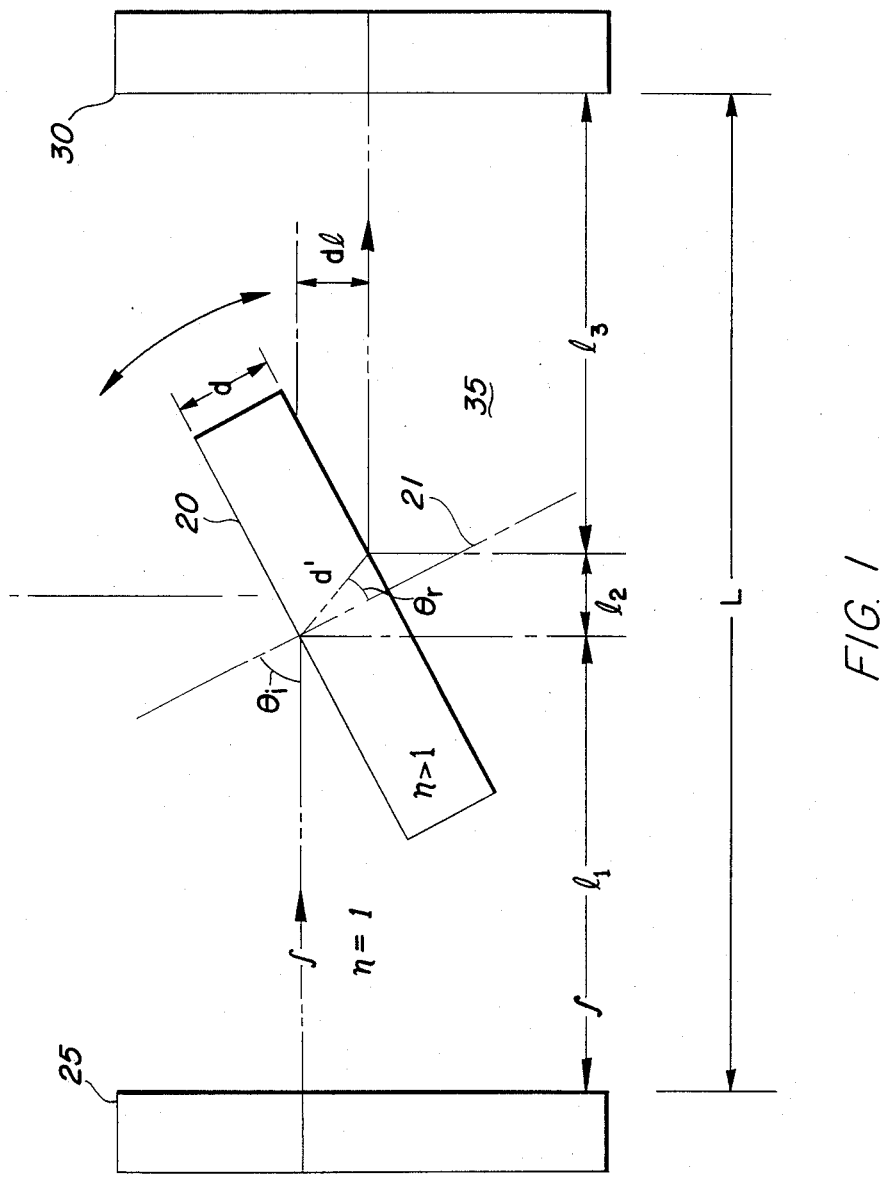
FIG. 1 is a schematic diagram showing a plate located in a passive plane cavity.

FIG. 1 is a highly schematic diagram of a spoiler plate 20 of thickness d located between two surfaces 25 and 30. The two surfaces 25 and 30 define a passive plane cavity 35. The cavity 35 is not the same cavity as the laser resonator cavity. Indeed, a laser is not shown at all in FIG. 1 to emphasize the distinction between this invention and other well-known uses of a Brewster plate within a laser resonator cavity.

The passive plane cavity 35 of FIG. 1 may be considered an accidental cavity in that it is formed by reflective surfaces such as a laser lens, a detector surface and other system surfaces. In FIG. 1, an optical length L is depicted between surfaces 25 and 30. The length L consists of $l_1$, $l_2$ and $l_3$. Plate 25 is shown at an angular position with respect to a horizontal axis. Refractive index, n, will vary depending upon the material involved. It is necessary to assign some relative values to the refractive index n of FIG. 1. Cavity 35 is assumed to be passive air with n=1, and plate 25 is any material transmitting the light wavelength of interest with n>1. The plate 20, as it oscillates from a normal to a horizontal position, increases the geometrical optical length of, for example, a laser light ray beam 22. Assume light beam 22 is retarded as it passes through plate 20. That retardation increases the effective geometrical optical length L of cavity 35. The amount of increase is controlled by the angle $\theta_r$ shown between dashed line 21 and d' in FIG. 1.

A series of mathematical equations of relevance to this invention may now be developed based upon the inventor's discoveries and having relevance to the schematic of FIG. 1. The analysis is relevant to the discovery that tunable diode lasers for use in spectroscopy are limited in effectiveness by interference fringes developed in the passive, or accidental, cavity 35.

Transmission of a normal-incident plane wave through two partially-reflecting plane-parallel surfaces separated by a distance L may be described by an Airy formula as follows:

$$T = 1/(1 + F \sin^2(2L\eta\nu)), \tag{1}$$

where F is the coefficient of finesse, $\eta$ the refractive index of the material between the surfaces, and absorption is neglected. As the laser frequency $\nu$, given in inverse-length units, is swept during a scan, the transmitted intensity therefore shows periodic intensity changes (fringes) whose maxima are separated by a frequency interval given by the free-spectral-range (FSR) of the cavity.

According to Equation (1), a maximum in the transmitted intensity will occur when $F \sin^2(2\pi L\eta\nu)$ equals zero, or when:

$$w\lambda = 2\eta L, \quad (2)$$

where w is an integer defining the order of interference.

The free-spectral range, which corresponds to a phase difference of 2, is given in units of Hz by:

$$FSR = c/(2L(\eta^2 - \sin^2\theta_i)^{\frac{1}{2}}), \quad (3)$$

where $\theta_i$ is the angle of incidence of the plane wave upon the cavity surfaces. For normal incidence, this reduces to:

$$FSR = c/2L\eta \quad (4)$$

The ratio of the FSR to the fringe half-width defines the finesse F* of the cavity:

$$F^* = (\pi F^{\frac{1}{2}})/2 = (\pi R^{\frac{1}{2}})/(1-R) \quad (5)$$

where R is the surface reflectivity. When a little care is taken in optical layout, and antireflection coatings are used, the observed fringes may be kept to 1% or less of the transmitted intensity. For fringes of low finesse, the transmission may be approximated:

$$T(\nu) = 1 - F/2 \, [1 - \cos(4\pi L\eta \infty)] \quad (6)$$

That is, the observed fringes, as indicated by the cosine term, are sinusoidal in nature. At this point one of the key features of this invention can be found from a review of Equation (6). The term of significance involves the understanding that observed fringes are dependent upon the variation of a term involving the length L and the light frequency.

It was discovered that a Brewster-plate spoiler would change the effective optical length L; and, since the sinusoidal nature is frequency-related, an oscillation of that plate washes out or spoils the interference fringes. Reduction of the interference fringes to a minimum increases the sensitivity of the tunable diode laser spectrograph and reveals scientific data that was, until the advent of this invention, almost totally masked by the interference fringes (See FIG. 5(c)).

A more detailed explanation of the nature of the invention may be appreciated with further reference to FIG. 1 and some additional mathematical equations applicable thereto. The theory underlying the Brewster-plate spoiler of this invention is considered further by using the foregoing assumptions of passive air for cavity 35 of FIG. 1 and $l_0$. A passive air ($\eta_0 = 1.0$) cavity of length $l_0$ bounded by partially-transmitting plane parallel surfaces 25, 30 is shown in FIG. 1. The addition of a Brewster plate 20 at an angle $\theta$ to the horizontal increases the optical pathlength from $\eta_0 l_0$ to:

$$L = \eta_0(l_0 - l_2) = d''\eta \quad (7)$$

where $\eta$ is the refractive index of the plate material. From FIG. 1 it can be seen that for a plate of thickness d:

$$d' = d/\cos\theta_r \quad (8)$$

and $$l_2 = d' \cos(\theta_i - \theta_r) \quad (9)$$

The optical pathlength L of the cavity may therefore be written:

$$L = \eta_0 l_0 - d'[\eta_0 \cos(\theta_i - \theta_r) + \eta)], \quad (10)$$

and as the angle $\theta_i$ is changed from $\theta_{i1}$ to $\theta_{i2}$, this length will increase (for $_0 = 1$) by an amount:

$$\Delta L = d_1'[\cos(\theta_{i1} - \theta_{r1}) + \eta] - d_2'[\cos(\theta_{i2} - \theta_{r2}) + \eta]. \quad (11)$$

The increase in optical pathlength of a cavity is related to an increase ($\Delta\nu$) in its resonant transmission frequency according to:

$$\Delta L/L = \Delta\nu/\nu \quad (12)$$

In order to average the periodic part of the transmitted intensity, the cavity must be spoiled by the Brewster element. A frequency-related term is represented in Equation (11). The spoiling must be a minimum amount of one-half of the cavity FSR. The required change in the optical pathlength is then given by Equation (11) for an air cavity as:

$$\Delta L_{min} = \gamma/4 \quad (13)$$

For wavelengths in the 3–20 μm region, the required change in pathlengths is only 0.75–5 μm. It may be that frequency changes of several FSRs will be optimum for fringe amplitude reduction, but even so, the corresponding pathlength changes required are readily achievable by the method and apparatus of this invention.

An interesting result of Equation (12) is the independence of $\Delta L_{min}$ on L. This means that provided the Brewster-plate spoiler is placed somewhere in the path between the two surfaces 25, 30 producing the interference fringes, it will do its job for any cavity length. This is a desirable characteristic and a significant feature for long-path atmospheric monitoring applications employing this invention.

Figure 2:
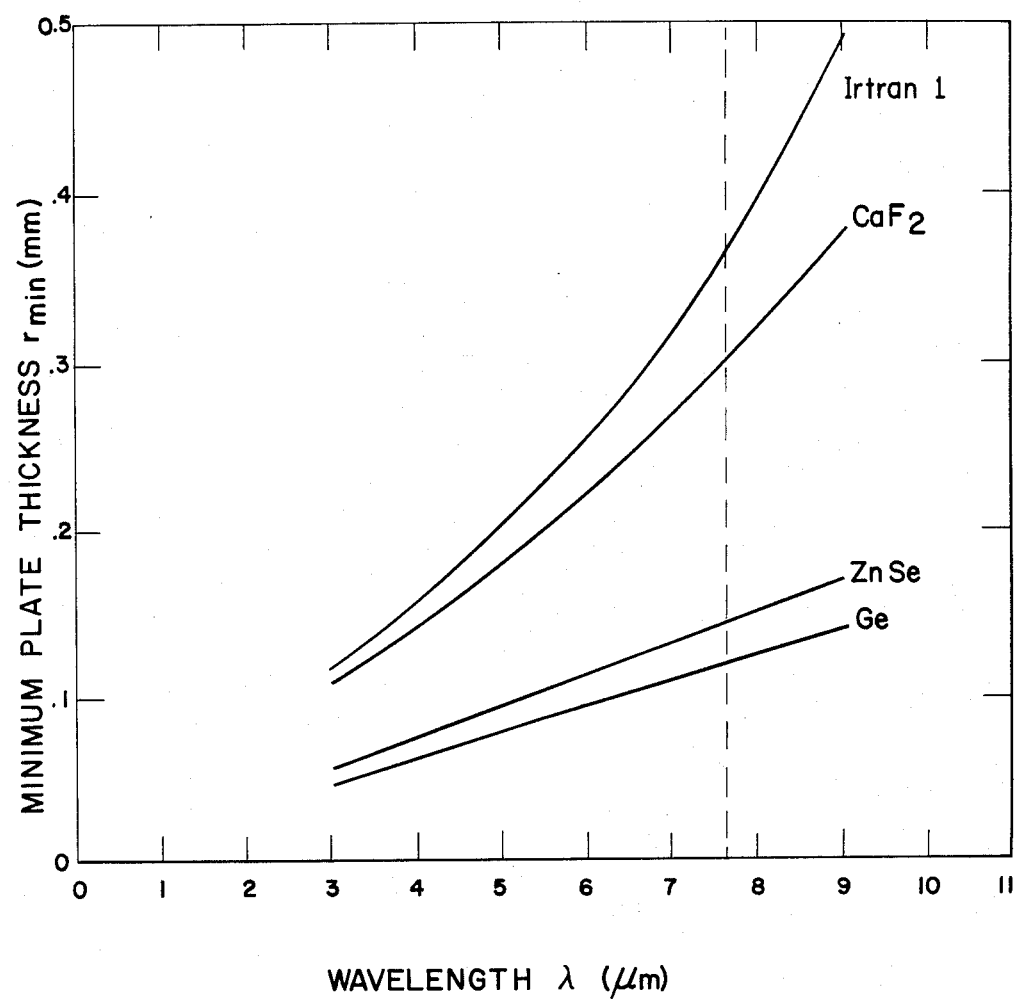
FIG. 2 depicts variation in refractive index with wavelength for various materials.

Equations (10) and (12) are used to calculate, for given wavelengths and material refractive indices, the minimum Brewster-plate thicknesses $r_{min}$ required to meet the criterion for averaging the fringes over an angle of oscillation of $\Delta\theta$. FIG. 2 depicts the minimum plate thickness required for fringe averaging using $\Delta\theta = 1°$ plotted for wavelengths in the range 3–10 m. For small values of $\Delta\theta$, $r_{min}$ is inversely proportional to $\Delta\theta$. FIG. 2 shows, for a given angle of oscillation ($\Delta\theta = 3°$), that a particular plate (Irtran 1) having a minimum thickness, $r_{min} = 0.105$ mm, is required at 7.65 μm for enhanced operational capabilities.

Figure 3:
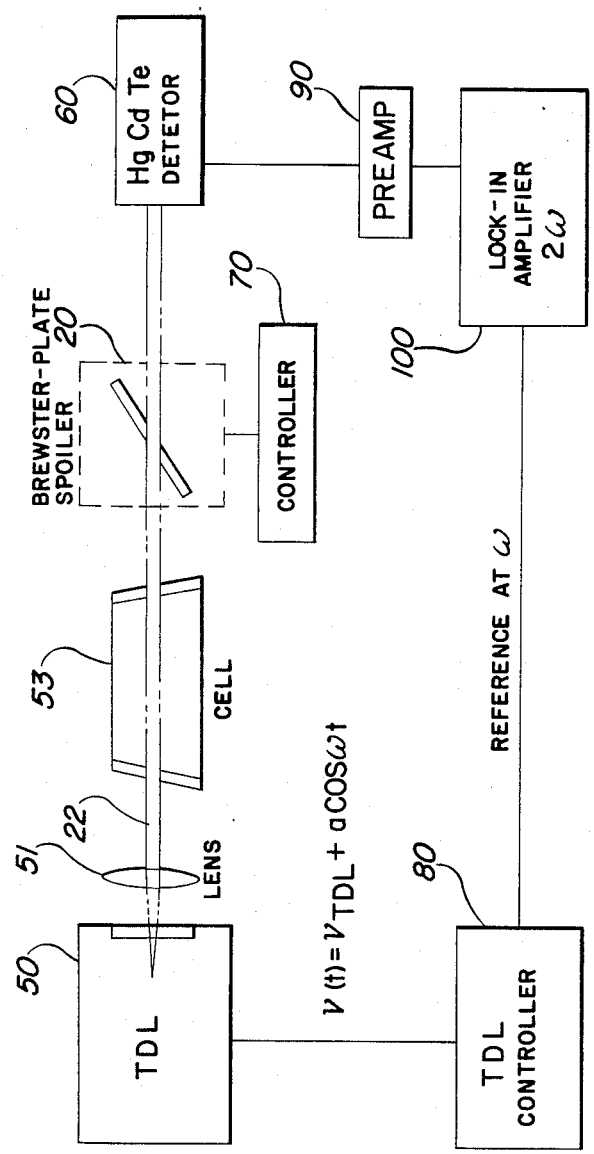
FIG. 3 is a schematic diagram of a short-path absorption system in accordance with this invention.

FIG. 3 depicts a preferred embodiment of this invention for a particular system environment. A stripe-geometry tunable diode laser ("TDL") 50 (supplied from Laser Analytics) operating at 7.65 μm and a HgCdTe detector 60, are operated in the system depicted in FIG. 3. The Brewster-plate spoiler 20 is a 1-mm thick, 25-mm diameter Irtran 1 window mounted on a galvanometer scanner (not shown) but of the type supplied from General Scanning Inc. Model G300PD. Controller 70 includes an amplifier (supplied from GSI Model CCX100) and a function generator (supplied from Wavetek). The function generator is selectively operable to provide square-wave, sine wave or triangular-wave functions at adjustable amplitudes and at frequencies up to a few hundred Hertz. In my discovery, I first established that the Brewster-plate spoiler 20, itself, did not contribute to any observed fringes. Afterwards, the spoiler 20 was permanently left in the beam 22 and it was turned on or off as needed to prove the merit of this invention. The diode laser 50 was modulated at 1.2 kHz by controller 80 with a peak-to-peak amplitude producing the maximum second-harmonic signal for the gas being studied, (N$_2$O). The output signal from detector 60 was amplified using a preamplifier 90 (supplied from IRA PPA-15-20) and after amplification was fed to a lock-in amplifier 100 (supplied by Ithaco Dynatrac 3). Obviously, the selected suppliers are merely representative and should not be construed or interpreted as limiting the scope or breadth of this invention.

The peak-to-peak optical depth of a fringe is F, or $(2F^*/\pi)^2$ in this approximation. The Finesse F* may now be written:

$$F^* \simeq \pi R^{\frac{1}{2}} \quad (14)$$

so that the peak-to-peak optical depth of the fringes may be approximated by 4R. Interference fringes of optical depth of 1% peak-to-peak may therefore be identified with a reflectivity of 0.0025 and finesse 0.16.

In derivative spectroscopy, the TDL output frequency $\nu_{TDL}$ is modulated from controller 80 by applying a small sinusoidal variation to the TDL current. The laser output frequency becomes:

$$\nu(t) = \nu_{TDL} + a \cos \omega t, \quad (15)$$

where $\omega$ is the angular modulation frequency, and a is half the peak-to-peak amplitude of the modulation. If the laser frequency in beam 22 is now tuned over an absorption lineshape with a line-center absorption at $\nu_0$, an offset frequency from line-center may be defined such that:

$$\nu_{TDL} = \nu_0 + \nu_1$$

or $$\nu(t) = \nu_0 + \nu_1 + a \cos \omega t. \quad (16)$$

The transmitted intensity as laser 50 scans through the interference fringes is then:

$$T(\nu,t) = 1 - F/2[1 - \cos(4\pi L(\nu_0 + \nu_1 + a \cos \omega t))]. \quad (17)$$

For the small modulation indices encountered in derivative detection, as is known, the peak-to-peak modulation amplitude applied to laser 50 is much less than the fringe period ("FSR"), and the signals detected at $\omega$, $2\omega$, $3\omega$, etc., are proportional to the derivatives $T'(\nu)$, $T''(\nu)$, $T'''(\nu)$, etc., of the transmitted intensity. In this case, $$T'(\nu) = [-F/2]4\pi L\eta \sin(4\pi L\eta\nu) \quad (18)$$

and $$T''(\nu) = [-F/2](4\pi L\eta)^2 \cos(4\pi L\eta\nu) \quad (19)$$

The harmonic response as the laser-frequency is swept is therefore also sinusoidal, but the fringes appear with a peak-to-peak amplitude less than F, as determined as the a-dependent proportionality constant.

For larger modulation amplitudes, the proportionality no longer holds valid, and the harmonic response at $\omega$, $2\omega$, $3\omega$, etc., can only be calculated from evaluation of the Fourier components of the modulated signal. The time-dependent term of the transmitted intensity is $T(\nu_0 + \nu_1 + a \cos \omega t)$ and is a periodic and an even function of $\omega t$ (time), which may therefore be expanded in a cosine Fourier series:

$$T(\nu_0 + \nu_1 + a\cos\omega t) = \sum_{n=0}^{\infty} H_n(\nu_0 + \nu_1) \cos n\omega t, \quad (20)$$

where $\nu_0 + \nu_1$ is considered a constant over the 1) period. $H_n(\nu_0 + \nu_1)$ is then the $n^{th}$ Fourier component of the modulated transmitted intensity. These dimensionless coefficients give the relative magnitude of the signals which are detected at the different harmonics of the modulation frequency.

The Fourier coefficients are then:

$$H_n(\nu,t) = \frac{2}{\pi} \int_0^\pi T(\nu,a)\cos n\theta d\theta,$$

$$= \frac{2}{\pi} \int_0^\pi \left[ 1 - \frac{F}{2}(1 - \cos(4\pi L\eta(\nu_0 + \nu_1 + a\cos\theta))) \right] \cos n\theta d\theta,$$

$$= \frac{F}{\pi} \int_0^\pi \cos(4\pi L\eta(\nu_0 + \nu_1 + a\cos\theta)) \cos n\theta d\theta \quad (21)$$

As is established above, it is the magnitudes of the Fourier coefficients $H_n(\nu,t)$ which determine the sizes of the harmonic responses at $\omega$, $2\omega$, $3\omega$, etc.

The interference fringes observed in a direct absorption (zero modulation) laser scan will have a fringe period given by the FSR (see Equation (2)). For molecular line detection, it is useful to define a modulation coefficient m, where:

$$m = a/\gamma \quad (22)$$

and $\gamma$ is the molecular linewidth (HWHM). For $m < 1$, derivative spectroscopic techniques are appropriate, while for $m > 1$ harmonic techniques must be used. For the detection of weak absorptions, the signal-to-noise ratio must be optimized by increasing m to maximize the peak heights of the harmonic signals. For Doppler lineshapes, $m_{max} = 1.65$ and 2.2 for first and second harmonic detection, respectively. For Lorentzian lineshapes, $m_{max} = 2.0$ and 2.2, respectively.

For sinusoidal (low finesse) interference fringes with a fringe period greater than the FWHM of the molecular lineshape, the observed fringes in the first- and second-harmonic spectra have a period also equal to the original fringe period, and $m_{max}$ is approximately unity. For interference fringes with a period much less than the molecular linewidth, the modulation technique will discriminate against them in intensity, but produce at $\omega$ and $2\omega 0$ apparent fringes of complex shape, whose period may be different from the original fringe period.

In the observed harmonic spectra, apparent fringes with periods much greater or smaller than the molecular FWHM can be easily removed with well-known filtering techniques, and such techniques are within the scope of this invention. A more difficult problem arises when the observed fringe period is similar to the molecular lineshape width. Indeed, the discriminating nature of the harmonic detection technique means that the fringes that do come through the standard demodulators/filters are more typically of just this fringe period. The worst case is when the molecular linewidth (FWHM) is equal to half of the fringe period.

When pressure broadening is negligible, the molecular lineshape may be described by Gaussian functions. The Gaussian linewidths (HWHM) range, for example, from 0.0007 cm$^{-1}$ (20 MHz) for $N_2O_5$ at 8 $\mu$m, to $\simeq$0.002 cm$^{-1}$ (60 MHz) for NO at 5 $\mu$m, for a gas temperature of 300K. Interference fringes of period equivalent to the 80–240-MHz range are typical for twice the midinfrared Doppler widths (FWHM). Resonator lengths which may be realistically encountered in low-pressure measurements lie in the range 190/$\eta$ to 63/$\eta$ centimeters. Even for high refractive index materials such as germanium, optical elements of these long lengths are usually not used. Air paths in the range 63–190 cm are determined to be responsible for troublesome fringing.

The method and apparatus of FIG. 3 relies on continuously changing the effective cavity length so that the above-described interference effects which produce the fringes are averaged during the laser wavelength scan. While this could be achieved by movement (oscillation) of an existing individual optical element, which is one of the surfaces defining the cavity, this approach is not nearly as practical as employing an oscillating plate. Moving one of the surfaces is particularly difficult if the laser diode itself or the detector element is involved. An oscillating Brewster-plate 20 is inserted at a convenient point in the beam 22 between the cavity surfaces which, in FIG. 3, are defined by the lens 51, the plates of cell 53 and the surface of detector 60. These surfaces will, in combination, define a passive cavity having an effective optical length L.

Cell 53 of FIG. 3, in my preferred embodiment, comprises a 15-cm-long cell with calcium fluoride windows and contains a very low pressure of $N_2O$. The cell 53 could be moved in or out of the beam. Spectral line identification and wavelength calibration is accomplished by using a 0.5-m spectrometer (Jarrell-Ash) and a 3-inch-long Germanium Etalon.

In practice with my invention, the gas cell 53 was first removed from beam 22. After optical alignment, the diode laser current was scanned from 0.13 to 0.19 A, as shown by the horizontal scale of FIG. 4. With spoiler 20 off (not oscillating), a large amplitude of a few percent, as shown by signal 41, is present. The interference has a measured FSR of 200 MHz. This measurement is in good agreement with that calculated (209 MHz) for an air cavity of geometric length of 0.72 m, the measured distance L of the cavity 35 between the window of TDL 50 and the window of the detector 60. Turning the Brewster-plate spoiler 20 "on," as depicted by waveshape 42 in FIG. 4, reduced the fringe peak-to-peak amplitude by a factor of about 30. For this result, $\theta_i$, FIG. 1, was about 4°.

Figure 4:
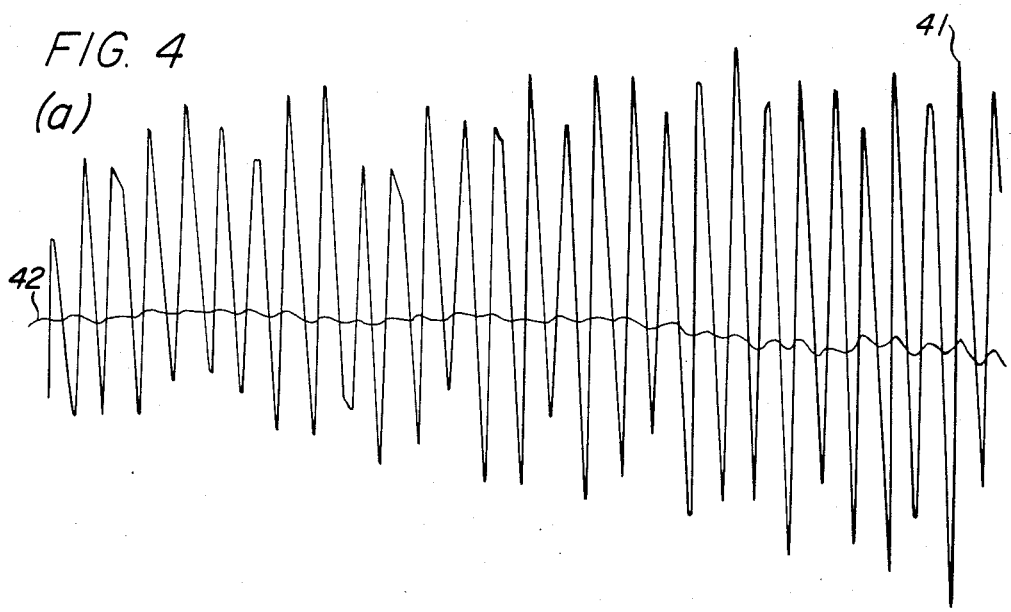
FIG. 4 is a diagrammatic sketch comparing oscillation functions with the spoiler on and off.
Figure 4:
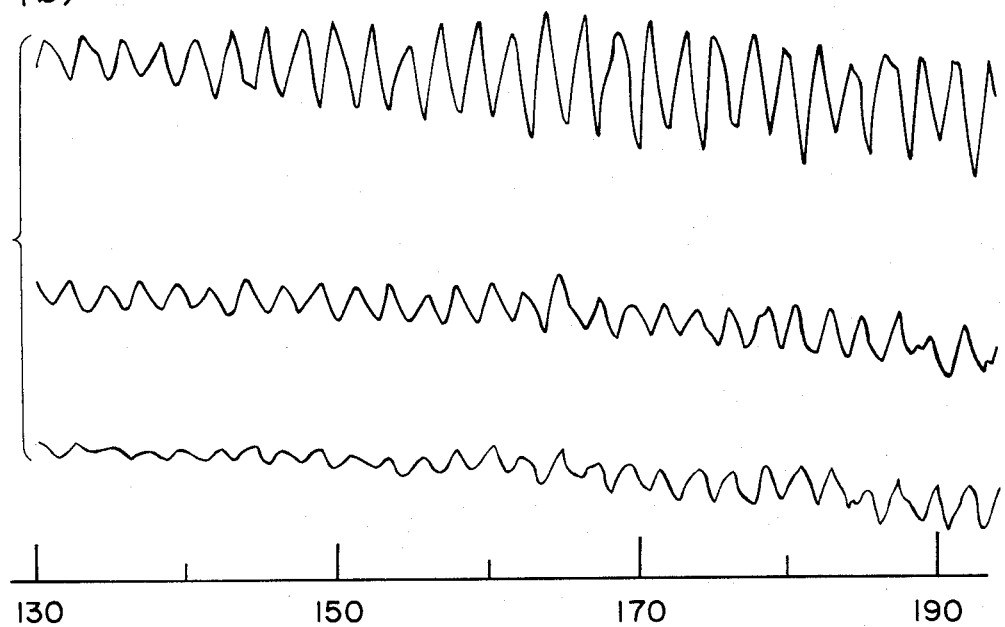

I investigated the dependence on $\Delta\theta$ by leaving the oscillation frequency for plate 20 set at 47 Hz and increasing the amplitude of the driving oscillation signal. For $\Delta\theta<0.4°$, corresponding to scanning through <0.5 FSR in frequency, the fringe averaging was poor, but increased rapidly for $\Delta\theta>0.4°$. Only little more improvement up to $\Delta\theta\simeq12°$, corresponding to scanning through about 16 FSR intervals during the oscillation, was noted. For $\Delta\theta>12°$, fluctuations in the lock-in amplifier output signal grew larger than the original observed fringes. For $\Delta\theta$ fixed at about 2°, corresponding to scanning through 2-3 FSRs, the oscillation waveform was changed, as shown in FIG. 4. The difference in these three traces is believed to result from the differing fraction of the period of oscillation spent at fixed plate locations. That is, the triangular wave oscillation produces a better averaging of the optical path than sine-wave oscillation with its turning points or square-wave with its two-position effect. These differences are reduced by scanning over an increasing number of cavity FSRs. The residual using triangular-wave oscillation, although not fully understood, is thought to arise from an effective rounding of the waveform at the turning points, whether the cause is electronic or mechanical in nature.

While the oscillating Brewster plate 20 reduces the unwanted fringe amplitude, it also causes signal amplitude modulation at the frequency of oscillation due to a combination of beam displacement at the detector and variations of the plate transmission with angle of incidence. This may become a problem when any component which comes through the signal-processing chain is comparable in size to the observed fringes. In such instances, the effectiveness of the spoiler plate is reduced. The frequency of plate oscillation must therefore be chosen carefully according to two criteria. First, it must cause an averaging of the fringe amplitude in a time less than the time taken for the TDL to scan over one-half of the fringe period. Secondly, this frequency and its harmonics must lie outside the effective bandpass of the lock-in amplifier which is set to the center frequency (in this case, 1.2 kHz). These criteria are easily met in the practice of my invention; and when met, the effectiveness of the spoiler plate greatly enhances the detection of frequencies of interest in a tunable diode absorption spectrum.

Figure 5:
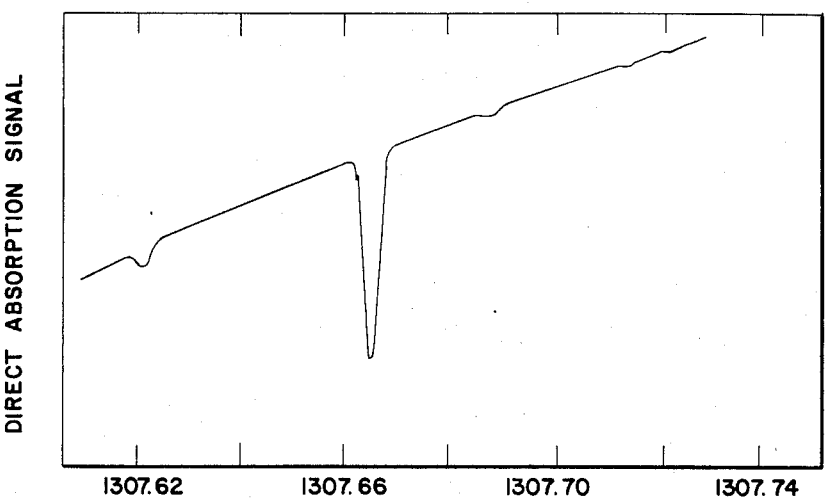
Figure 5:
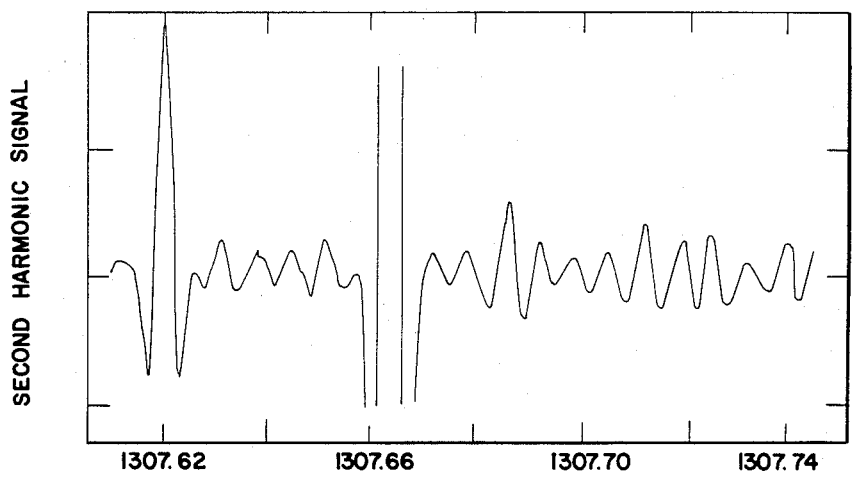
Figure 5:
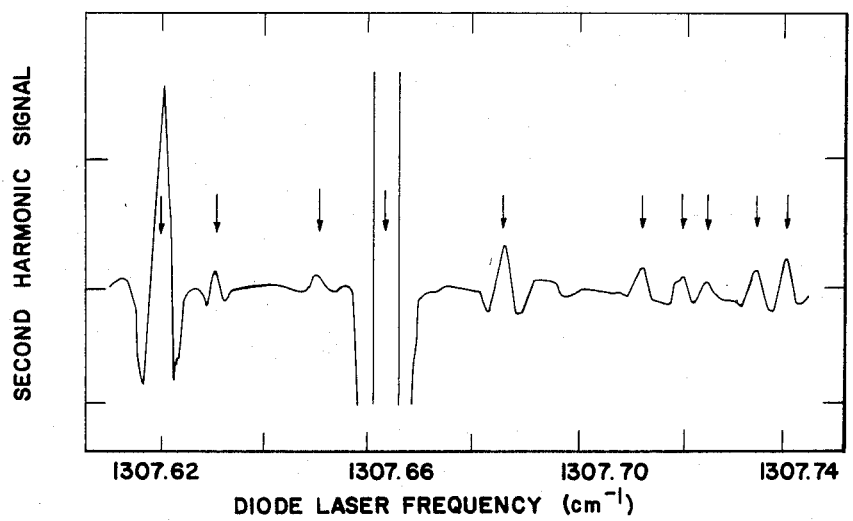

FIG. 5 shows the Brewster-plate spoiler's use in a direct absorption spectrum of low-pressure $N_2O$. The peak-to-peak fringe amplitude in trace (b) of FIG. 5 is about 0.5% of the transmitted intensity. Only when the Brewster-plate spoiler is turned on (trace (c)) are the fringes reduced to a sufficiently low level to allow weak lines (indicated by arrows) to be identified. The merit of my invention is shown by comparison of the waveforms of FIG. 5(b) with FIG. 5(c). Without my invention, the weak lines at the arrows of FIG. 5(c) are not visible in FIG. 5(b).

The ultimate test of any fringe-reducing technique is to improve the present limits of sensitivity of absorption techniques. Those limits were significantly improved by employment of my invention. The optical elements, arranged as shown in FIG. 3, were first carefully positioned to minimize any observed fringing with the spoiler plate 20 turned "off." With the detector dewar turned a few degrees away from normal incidence, the fringing could be reduced in amplitude to a peak-to-peak height equivalent to the size of a second harmonic signal resulting from an $N_2O$ line of peak absorption 0.01%. The scale calibration was done by recording the size of second harmonic $N_2O$ profiles resulting from lines whose peak absorptances measured directly were 5% and 1%.

Figure 6:
FIG. 6 is a series of graphs of various signal contributions in the absence of an absorbing molecular gas and the peak second harmonic signal size that an $N_2O$ feature of the peak absorptance would have if simultaneously recorded.
Figure 6:
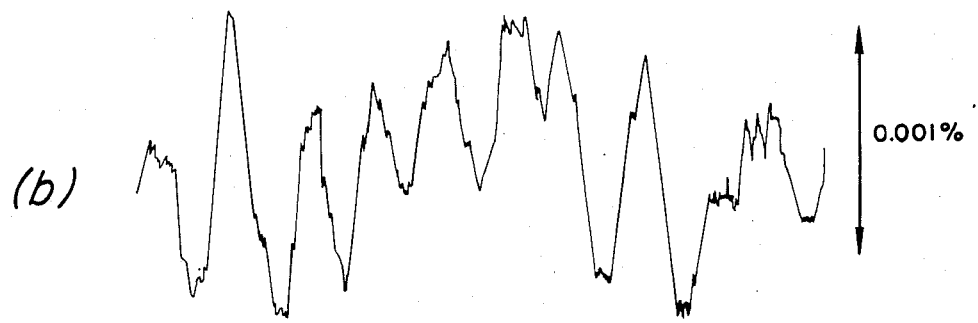
Figure 6:
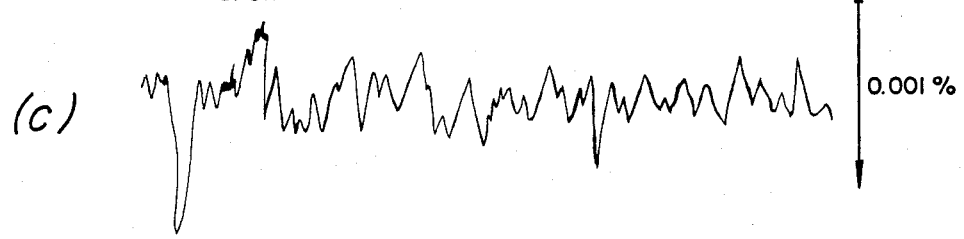
Figure 6:
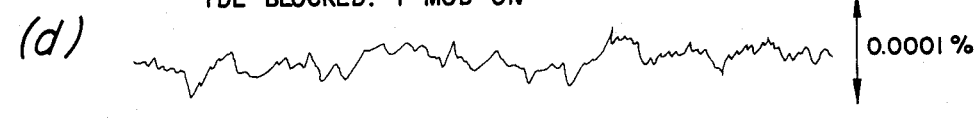

With the spoiler on in the absence of $N_2O$ (see FIG. 6(b)), the rms background signal was below the peak-to-peak size of the second harmonic signal of a 0.001% or 1 in $10^5$ line-center absorptance. This background signal was made up of two main contributions, one from optical fringing and the other from optical beam noise. The latter could be measured by scanning the diode laser current with zero current modulation to the laser (trace (c)). The detector-plus-amplifier noise, shown in FIG. 6(d), is an order of magnitude smaller than either the optical beam noise or the residual fringes. As expected, the optical beam noise, which is the random amplitude noise superimposed on the TDL beam, reduces by a factor $\pi^{\frac{1}{2}}$ as the integration time $\tau$ is increased. This is, of course, not true for the optical fringing. Trace (c) in FIG. 6 shows that the background recorded in trace (b) for a 1.25 second time constant is approximately equally-weighted by optical beam noise and fringing contributions. It should be noted that the optical beam noise background recorded in (c) was unchanged when the spoiler was turned on.

Fringe averaging is thus achieved by oscillating the Brewster plate about the Brewster's angle position. For sinusoidal and square-wave oscillation, the plate spends more time at its extreme positions than at its mid-position. Fringe spoiling may therefore not be completely achieved. In my preferred embodiment, the Brewster plate is driven by a triangular-wave oscillation signal. A triangular-wave oscillation which is several times the frequency of the FSR is advantageous for optimum fringe reduction.

Brewster's angle operation of the plate is chosen to maximize the insertion losses when polarized lasers are used. In addition, the faster tuning capability at larger angles of incidence requires a thinner plate and therefore less beam displacement and aberrations.

I have discovered that the further the plate angle is from normal incidence, the smaller the intensity modulation of the transmitted beam due to multiple-beam interference within the plate itself. Even at Brewster's angle, however, interference effects will occur for waves of E-vector perpendicular to the plane of incidence. For a 5-mm-diameter TDL beam at 765 μm impinging on a 1-mm plate at Brewster's angle, a fraction $1-(2d \tan \theta_r)/5$ of the beam reflected from the second surface will overlap with that reflected from the first. The interference fringes generated by the scanning laser will, however, have a FSR of several cm$^{-1}$. Accordingly, the interference fringes will not be observed during spectroscopic measurements over features 100 times narrower.

The beam displacement following the insertion of the Brewster plate into the optical path, and also during the plate oscillation, can be calculated. For an angle of incidence $\theta_i$, the beam displacement dl for a plate of thickness d (see FIG. 1) is:

$$dl = d \sin(\theta_i - \theta_r)/\cos \theta_r \qquad (23)$$

For example, when a 1-mm thick plate of refractive index 1.27 (Irtran 1) is inserted at Brewster's angle of 51.78° in a beam of wavelength 7.65 μm, the beam is displaced by 298 μm. An oscillation of ±1° about this angle then produces a change of 21.5 μm in the displacement. If germanium were used instead, the initial displacement is larger (dl ≃910 μm), but the change due to a ±1° oscillation about Brewster's angle (75.99°) is similar (16 μm).

Suitable choice of plate material makes this invention applicable for all wavelength regions from UV to far-IR. In the visible region, for example, at 590 nm, a fused silica plate ($\eta = 1.458$) of thickness 0.315 mm is at a Brewster's angle of 55.56° to average interference fringes by oscillation over an angle $\Delta\theta > 1°$. Considering the fragility of a 0.3-mm plate, however, it may be preferable to use a thicker plate and oscillate over a smaller angle.

For multipass cells, interference effects arise between adjacent spots on the field mirror. The cavity length which determines the FSR is twice the base length of the cell. In order to reduce multiple-beam interference, the Brewster-plate spoiler must be put in the multipass location and mounted in a location such that all beams pass through the plate. In the visible region, the plate might be a microscope slide, for example.

Monochromators or spectrometers find widespread use in TDL spectroscopic monitoring and are often a source of unwanted fringes. The fringes are formed by reflections between coupled surfaces, such as the source and entrance slit, or the exit slit and detector. An oscillating Brewster plate, in accordance with this invention, is a simple solution for fringe reduction. The use of a Brewster-plate spoiler substantially improves the overall fringe reduction attainable using only a single plate. Furthermore, two asynchronously-driven plates may be mounted so that the second plate compensates for any gross beam displacement caused by insertion of the first plate into the laser beam.

FIG. 3 depicts a first plate 20 and controller 70 together with a second plate 23 and its controller 71. The second plate 23 will be controlled in a manner to compensate for any bear displacement due to the pressence of plate 20.

The above description presents the best mode contemplated in carrying out my invention. My invention is, however, susceptible to modifications and alternate constructions from the embodiments shown in the drawings and described above. Consequently, it is not the intention to limit the invention to the particular embodiments disclosed. On the contrary, the invention is intended and shall cover all modifications, sizes and alternate constructions falling within the spirit and scope of the invention, as expressed in the appended claims when read in light of the description and drawings.

What is claimed is:

1. A method of reducing interference fringes created in a passive cavity defined by partially-transmissible optical surfaces compromising the steps of:
    placing at least one Brewster-plate spoiler in the cavity to increase the optical path length of a beam; and
    oscillating the Brewster-plate back and forth over an angle which causes the cavity resonances to tune in frequency over a range which corresponds to several times the period of the interference fringes.

2. A method in accordance with claim 1 and comprising the additional step of:
    driving the Brewster-plate spoiler with a triangular oscillation signal.

3. A method in accordance with claim 1 and comprising the additional step of:
    driving the Brewster-plate spoiler with a square-wave oscillation signal.

4. A method in accordance with claim 1 and comprising the additional step of:
    driving the Brewster-plate spoiler with a sine-wave oscillation signal.

5. A method in accordance with claim 1 wherein the passive cavity has a free-spectral-range (FSR) with fringes whose maxima are separated by a specific frequency and comprising the additional step of:

oscillating the plate at a minimum amount of one-half of the FSR of the cavity.

6. A method in accordance with claim 5 and comprising the additional step of:
reducing the interference fringes by oscillating the plate by an amount producing a change in the cavity resonant frequency which is typically several times, and at least one-half, of the FSR of the cavity.

7. A method in accordance with claim 1 and comprising the additional step of:
orienting the Brewster-plate in said beam at the Brewster angle.

8. A method in accordance with claim 1 wherein said placing and oscillating steps are further characterized by the step of:
asynchronously oscillating at least a pair of Brewster-plate spoilers in said cavity.

9. Apparatus for reducing interference fringes which are present in a passive cavity defined by partially-transmissible optical surfaces in a tunable laser absorption spectrometer, said apparatus comprising:
a transmissive plate means adapted for oscillation and located in the laser's optical beam; and
means for oscillating said plate means over an angle selected to cancel the interference fringes.

10. Apparatus in accordance with claim 9 and further comprising:
a tunable diode laser emitting a laser beam for absorption in a molecular substance to be measured.

11. Apparatus in accordance with claim 10 wherein said passive cavity is defined by surfaces such as, but not limited to, a laser optical exit plate, a detector input plate, and further wherein said apparatus is characterized in that:
transmission of a normal-incident plane wave of a laser beam through two partially-reflecting plane-parallel surfaces of said cavity separated by a distance L is described by an Airy formula as follows:

$$T = 1/(1 + F \sin^2(2\pi L \eta \nu)),$$

where F is the coefficient of finesse, $\eta$, the refractive index of the plate material between said cavity surfaces, absorption is neglected, and the laser frequency, $\nu$, is given in inverse-length units.

12. Apparatus in accordance with claim 11 wherein the tunable laser is swept during a scan and further characterized in that:
interference fringes exhibit periodic intensity changes whose maxima are separated by a frequency interval given by the free-spectral-range (FSR) of said cavity.

13. Apparatus in accordance with claim 12 and further characterized in that:
a maximum in the transmitted intensity of said fringe occurs when $F \sin^2(2\pi L \eta \nu)$ equals zero, or when:

$$w\lambda = 2\eta L,$$

where w is an integer defining the order of interference, $\eta$ is the refractive index of said plate, and L is the geometrical optical length of said cavity.

14. Apparatus in accordance with claim 13 and further characterized in that:
interference fringes are sinusoidal in nature and the amplitude of oscillation of said plate means is selected to nullify the amplitude of said interference fringes.

15. Apparatus in accordance with claim 14 and further comprising:
a source emitting a triangular oscillation signal; and
means for driving the plate means with said triangular oscillation signal.

16. Apparatus in accordance with claim 14 and further comprising:
a source emitting a square-wave oscillation signal; and
means for driving the plate means with a square-wave oscillation signal.

17. Apparatus in accordance with claim 14 and further comprising:
a source emitting a sine-wave oscillation signal; and
means for driving the plate means with said sine-wave oscillation signal.

18. Apparatus in accordance with claim 9 wherein said plate means is further characterized as:
a Brewster-plate located at a Brewster angle.

19. Apparatus in accordance with claim 18 and wherein said plate means further comprises:
a second Brewster-plate located in the laser's optical beam; and
means for asynchronously oscillating said second plate relative to the oscillation of said first plate.

* * * * *